(12) United States Patent
Sliski et al.

(10) Patent No.: US 7,109,505 B1
(45) Date of Patent: Sep. 19, 2006

(54) SHAPED BIOCOMPATIBLE RADIATION SHIELD AND METHOD FOR MAKING SAME

(75) Inventors: Alan P. Sliski, Lincoln, MA (US); Kenneth J. Harte, Carlisle, MA (US)

(73) Assignee: Carl Zeiss AG, Oberkochen (DE)

(*) Notice: Subject to any disclaimer, the term of this patent is extended or adjusted under 35 U.S.C. 154(b) by 0 days.

(21) Appl. No.: 09/502,762

(22) Filed: Feb. 11, 2000

(51) Int. Cl.
*G02B 5/00* (2006.01)

(52) U.S. Cl. .................... 250/505.1; 250/506.1

(58) Field of Classification Search ........ 250/505.1, 250/519.1; 378/65
See application file for complete search history.

(56) References Cited

U.S. PATENT DOCUMENTS

| | | | |
|---|---|---|---|
| 3,752,990 A | 8/1973 | Fischer | |
| 4,186,751 A | 2/1980 | Fleischmann | |
| 4,646,338 A | 2/1987 | Skillicorn | |
| 4,694,480 A | 9/1987 | Skillicorn | |
| 4,968,305 A * | 11/1990 | Takahashi et al. | 604/232 |
| 5,012,114 A * | 4/1991 | Sisson, Jr. | 250/519.1 |
| 5,090,043 A | 2/1992 | Parker et al. | |
| 5,153,900 A | 10/1992 | Nomikos et al. | |
| 5,165,093 A | 11/1992 | Miller et al. | |
| 5,369,679 A * | 11/1994 | Sliski et al. | 378/65 |
| 5,566,221 A * | 10/1996 | Smith et al. | 378/145 |
| 5,618,266 A * | 4/1997 | Liprie | 604/21 |
| 5,621,780 A | 4/1997 | Smith et al. | |
| 5,748,699 A | 5/1998 | Smith | |
| 6,099,457 A | 8/2000 | Good | |
| 6,181,770 B1 * | 1/2001 | Ciravolo et al. | 378/117 |

* cited by examiner

*Primary Examiner*—Nikita Wells
*Assistant Examiner*—Anthony Quash
(74) *Attorney, Agent, or Firm*—Mark G. Lappin; Greenberg Traurig LLP (57) ABSTRACT

A radiation applicator system is structured to be mounted to a radiation source for providing a predefined dose of radiation for treating a localized area or volume, such as the tissue surrounding the site of an excised tumor. The applicator system includes an applicator and an adapter. The adapter is formed for fixedly securing the applicator to a radiation source, such as a radiosurgery system which produces a predefined radiation dose profile with respect to a predefined location along the radiation producing probe. The applicator includes a shank and an applicator head, wherein the head is located at a distal end of the applicator shank. A proximate end of the applicator shank couples to the adapter. A distal end of the shank includes the applicator head, which is adapted for engaging and/or supporting the area or volume to be treated with a predefined does of radiation. The applicator can include a low energy radiation filter inside of the applicator head to reduce undesirable low energy radiation emissions. A biocompatible radiation shield may be coupled to the outer surface of the applicator head to block radiation emitted from a portion of the radiation probe, in order to shield an adjacent location or vital organ from any undesired radiation exposure. A plurality of applicators having applicator heads and radiation shields of different sizes and shapes can be provided to accommodate treatment sites of various sizes and shapes.

20 Claims, 6 Drawing Sheets

SHAPED BIOCOMPATIBLE RADIATION SHIELD AND METHOD FOR MAKING SAME

REFERENCE TO RELATED APPLICATIONS

This application is related to U.S. patent application Ser. No. 09/502,759, filed Feb. 11, 2000, now U.S. Pat. No. 6,421,416 and U.S. patent application Ser. No. 09/502,273, filed Feb. 11, 2000, now U.S. Pat. No. 6,301,326.

STATEMENT REGARDING FEDERALLY SPONSORED RESEARCH

Not Applicable

REFERENCE TO MICROFICHE APPENDIX

Not Applicable

BACKGROUND OF THE INVENTION

This invention relates to a miniaturized, programmable radiation source for use in delivering substantially constant or intermittent levels of x-rays to a specified region and, more particularly, to an apparatus for delivering a controlled dose of radiation to a localized volume of tissue, such as a volume of tissue of the human body.

In the field of medicine, radiation is used for diagnostic, therapeutic and palliative treatment of patients. The conventional medical radiation sources used for these treatments include large fixed position machines such as linear accelerators ("LINACs"), smaller transportable radiation delivery machines such as high-dose-rate after loaders, and catheters for low-dose-rate brachytherapy. The current state of the art treatment systems utilize computers to generate complex treatment plans for treating complex geometric volumes.

Typically, these systems apply doses of radiation in order to inhibit the growth of new tissue because it is known that radiation affects dividing cells more than the mature cells found in non-growing tissue. Thus, the regrowth of cancerous tissue in the site of an excised tumor can be treated with radiation to prevent the recurrence of cancer. Alternatively, radiation can be applied to other areas of the body to inhibit tissue growth, for example the growth of new blood vessels inside the eye that can cause macular degeneration.

Conventional radiation treatment systems, such as the LINAC used for medical treatment, utilize a high power remote radiation source and direct a beam of radiation at a target volume, such as a tumor inside the body of a patient. This type of treatment is referred to as teletherapy because the radiation source is located a predefined distance, typically on the order of one meter, from the target. This treatment suffers from the disadvantage that tissue disposed between the radiation source and the target is exposed to radiation.

An alternative treatment system utilizing a point source of radiation is disclosed in U.S. Pat. No. 5,153,900 issued to Nomikos et al., owned by the assignee of the present application, which is hereby incorporated by reference. The system includes a miniaturized, insertable probe capable of producing low power radiation in predefined dose geometries or profiles disposed about a predetermined location. One advantage of this system is that the radiation is applied to treat a predefined tissue volume, without significantly affecting the tissue in adjacent volumes.

A typical use of the described radiation therapy system involves positioning the insertable probe into or adjacent to the tumor or the site where the tumor or a portion of the tumor was removed to treat the tissue adjacent the site with radiation. In order to facilitate controlled treatment of the site, it is desirable to support the tissue portions to be treated at a predefined distance from the radiation source. Alternatively, where the treatment involves the treatment of surface tissue or the surface of an organ, it is desirable to control the shape of the surface as well as the shape of the radiation field applied to the surface.

The treatment can involve the application of radiation, either continuously or intermittently, over an extended period of time. Therefore, it is desirable that the insertable probe be adjustably supported in a compliant manner to accurately position the radiation source with respect to the treated site and accommodate normal minor movements of the patient, such as movements associated with breathing.

Accordingly, it is an object of the present invention to provide an improved system for delivering radiation to a localized region.

SUMMARY OF THE INVENTION

The present invention is directed to a biocompatible radiation shield for use with a radiation applicator system, which is mountable to a radiation source in order to apply a predefined dose of radiation to an area or volume. The radiation applicator system includes an applicator and adapter. The adapter couples the applicator to a radiation source. The applicator includes an applicator shank and an applicator head. The adapter engages the applicator shank at the shank' proximal end and thereby allows coupling of the applicator to the radiation source, when the adapter is coupled to the radiation source. At the opposite and distal end of the applicator shank is the applicator head, which is used for applying a predefined dose of radiation across a surface contour to treat a predefined volume of tissue surrounding a surgical site. Preferably, the applicator head and surface contour coincide such that the surface of the applicator head engages and/or supports the area or volume to be treated and applies a uniform dose of radiation over the area or volume to be treated.

The radiation shield is preferably formed to a predefined shape and size and adapted to be coupled to the applicator head in a predefined location in order to shield predefined portions of the treatment area or volume from radiation or to define the shape of the dose of radiation applied to the treatment area or volume. The biocompatible radiation shield is substantially thin and can be coupled to the surface of the applicator head, forming a thin shielding layer between the applicator head and the area or volume to be treated. The radiation head could also be integral with another material that is disposed, at least in part, over the applicator head or could be integral with the applicator head. The applicator head and shield combination can engage and/or support the area or volume that is shielded from the radiation.

In one embodiment, the radiation source includes an elongated probe and is adapted for producing a predefined radiation dose profile about a predetermined location with respect to the probe. In the this embodiment, the applicator system can also include a low energy radiation filter adapted to surround at least a portion of the probe within the applicator head. The low energy radiation filter serves to reduce the low energy radiation produced by the probe which can damage tissue adjacent the applicator head. The applicator head engages and/or supports the area or volume to be treated, such as the area or volume adjacent the site where a tumor was removed in order to permit the application of radiation to prevent the regrowth of the tumor. The radiation shield can be fastened to any portion of the applicator head that may, during treatment, be adjacent a location (such as a vital organ), in which the application of radiation is undesirable.

Preferably, the applicator system (and radiation shield) are adapted to be mounted to the elongated probe of the radiation source to form a self contained treatment assembly. During the surgical procedure, the treatment assembly including the applicator system and radiation shield and the radiation source can be supported by a carrier system. The carrier system can be adapted to support the treatment assembly in a substantially weightless configuration in order to facilitate positioning by the physician during surgery and to accommodate substantially minor movements by the patient, such as breathing.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

Figure 1A:
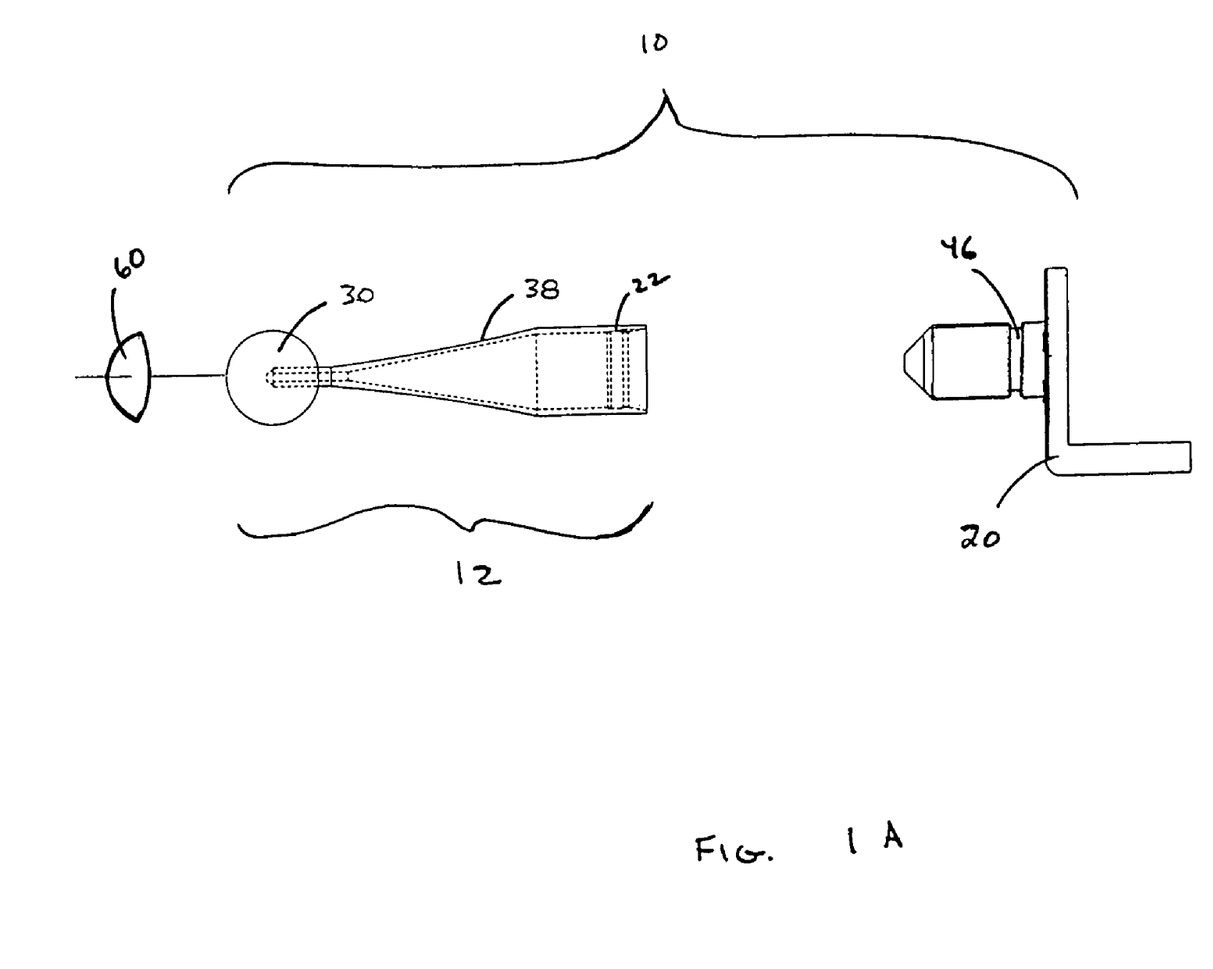
FIG. 1A is a diagrammatic exploded view of an applicator system with radiation shield, in accordance with the present invention.

FIG. 1A shows an applicator system 10 and a biocompatible radiation shield 60 for applying a dose of radiation to an area to treat a volume of tissue. The applicator system 10 includes an applicator 12 and an adapter 20. Applicator 12 includes a shank 38 and a head 30, wherein head 30 is located at a distal end of shank 38. A proximal end of shank 38 removably engages with adapter 20 to form applicator system 10. Wherein adapter 20 is structured for attaching applicator system 10 to a radiation source (not shown). At the opposite and distal end of applicator shank 38, applicator head 30 is adapted for engaging and conforming a tissue cavity to a desired shape in order to permit the area or volume adjacent the tissue cavity to be treated with a predefined dose of radiation.

The biocompatible radiation shield 60 is fastened to the applicator head 30 in order to shield a portion of the treatment area or volume from the dose of radiation. The shape of the applicator head 30 can be selected to closely approximate the shape of the cavity to be treated and the radiation shield 60 can be formed to conform to the shape or contour of the portion of the applicator head where the radiation shield is to be fastened. The applicator system 10 can also include a low energy filter (not shown) for absorbing or blocking low energy radiation.

Figure 1B:
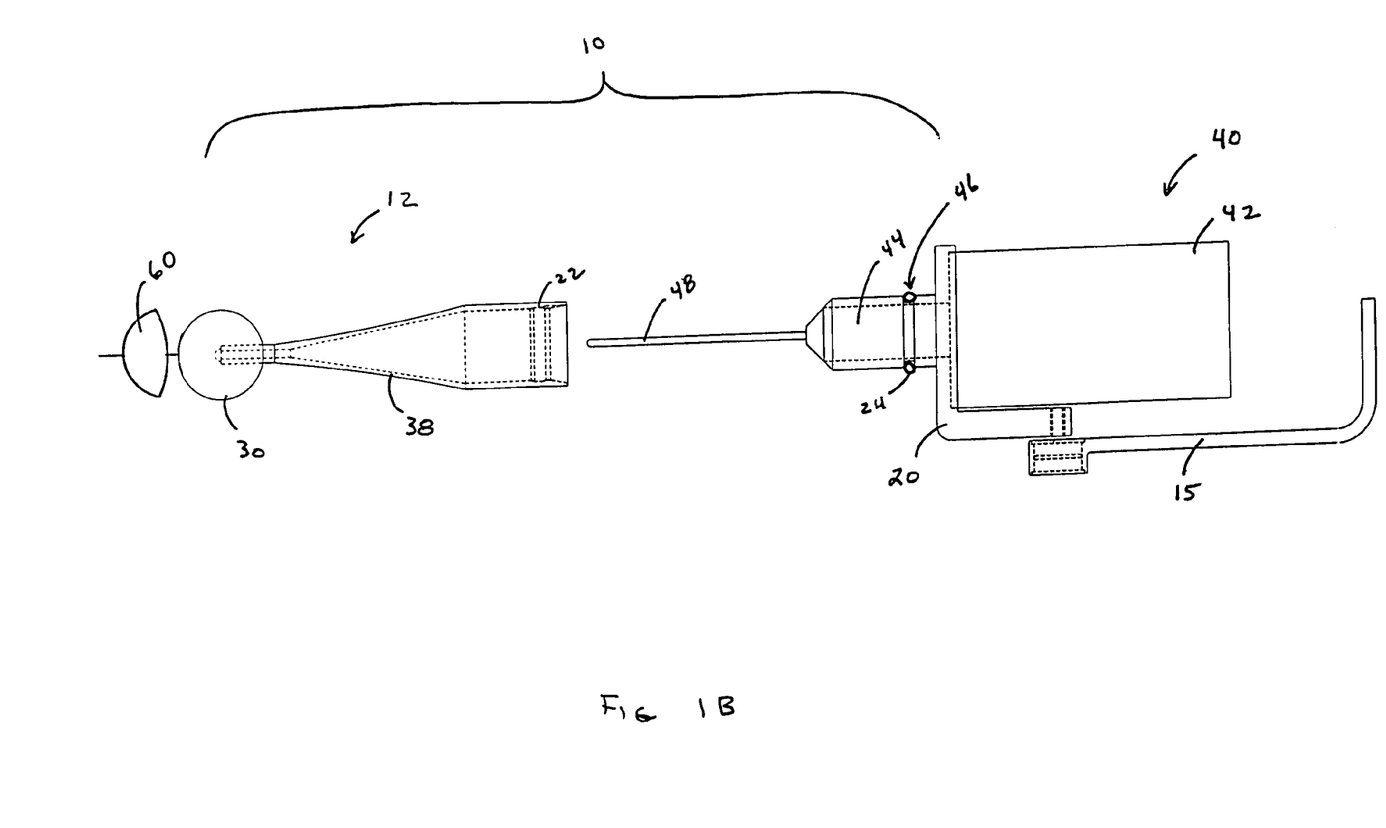
FIG. 1B is a diagrammatic exploded view of the applicator system and radiation shield of FIG. 1A and a prior art radiation source, with the applicator system adapter coupled to the radiation source.

FIG. 1B shows adapter 20 of application system 10 mounted on a radiation source, such as a radiosurgery system 40. The radiosurgery system 40 includes a housing 42, a barrel 44 and an elongated probe 48. The radiosurgery system 40 is adapted for generating a field of radiation having a predefined dose profile about the distal end of the probe 48. The applicator system 10 is adapted to fit over the probe 48 and the barrel 44 of the radiosurgery system 40.

In the embodiment shown, adapter 20 of the applicator system 10, which is supported by a carrier system arm 15, includes a circumferential groove 46 and a retaining spring 24 (or O-ring) mounted in groove 46. A portion of spring 24 extends above the surface of the adapter 44 to facilitate engagement of applicator 12 to adapter 20. The proximal end of the applicator shank 38 is adapted to fit over adapter 20 and includes an interior, circumferential groove 22 which is adapted to receive the portion of the spring 24 that extends above the adapter groove 46.

Figure 2A:
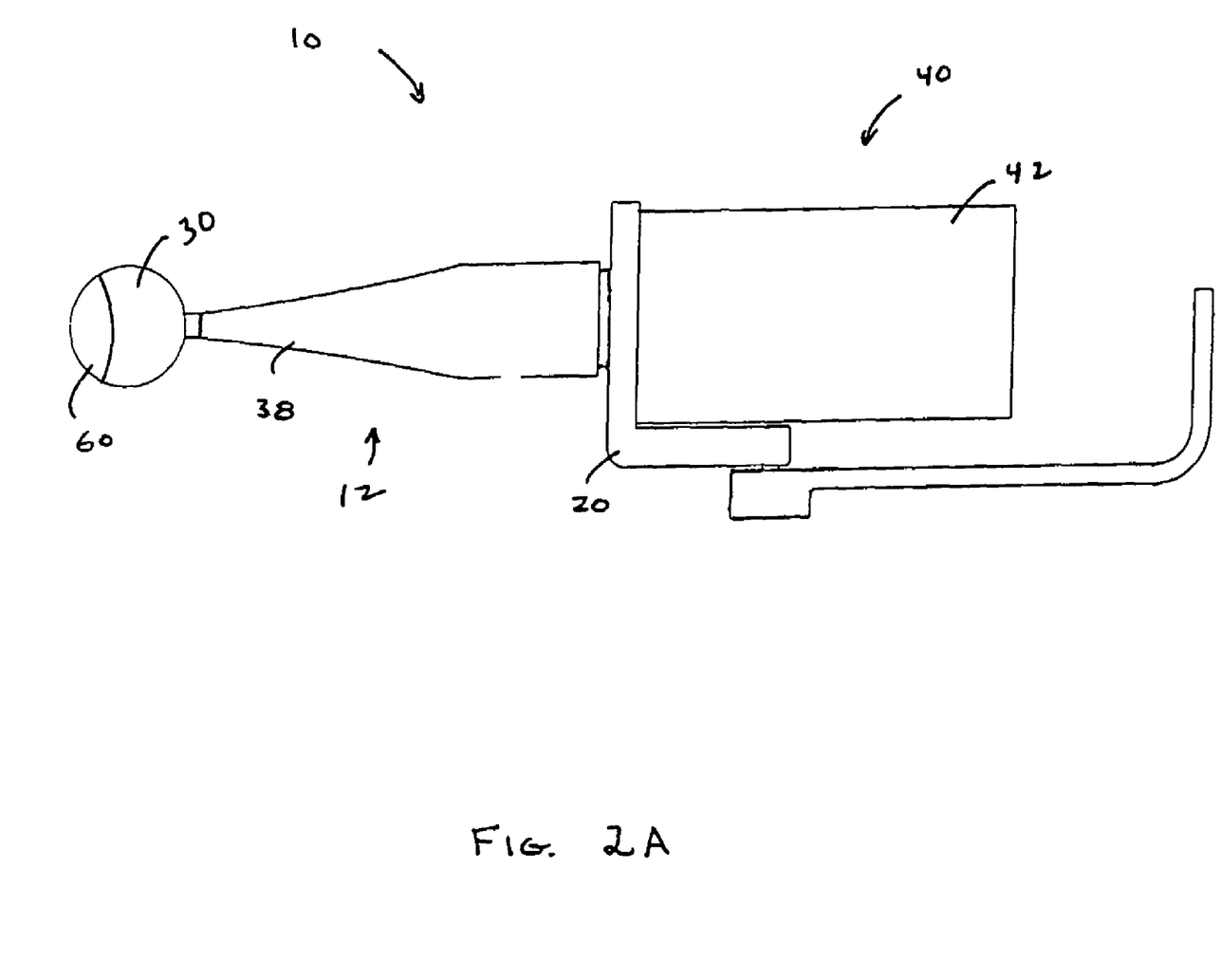
FIG. 2A is a diagrammatic view of the applicator system with the radiation shield and radiation source of FIG. 1B in assembled form.
Figure 2B:
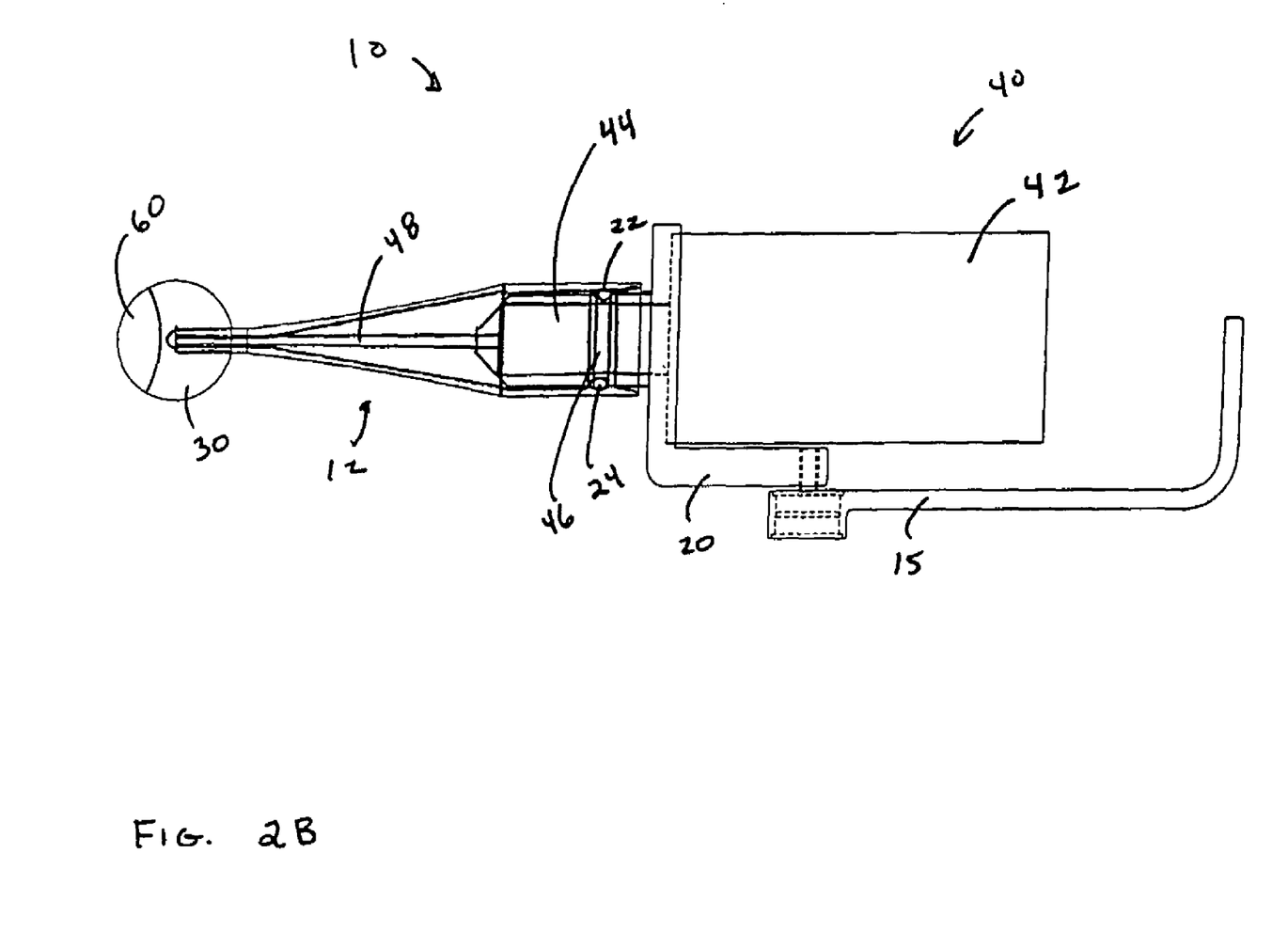
FIG. 2B is a diagrammatic view showing a cross-section of the applicator system with the radiation shield mounted to the radiation source of FIG. 2A.

As shown in FIGS. 2A and 2B, the applicator 12 slidably fits over and couples to adapter 20, which is secured to radiosurgery system 40. When applicator 12 is slid on to adapter 20 spring 24 is compressed by the interior surface of shank 38 and, once groove 22 aligns with spring 24, the spring expands to fill groove 22, thereby securely coupling shank 38 of applicator 12 to adapter 20. Consequently, applicator 12 is secured over probe 48 of the radiosurgery system 40. As a person having ordinary skill will appreciate, other well known coupling methods and mechanisms can be used, for example: a bayonet coupling, a threaded coupling, spring loaded ball bearings and detents, and set screws.

Figure 3:
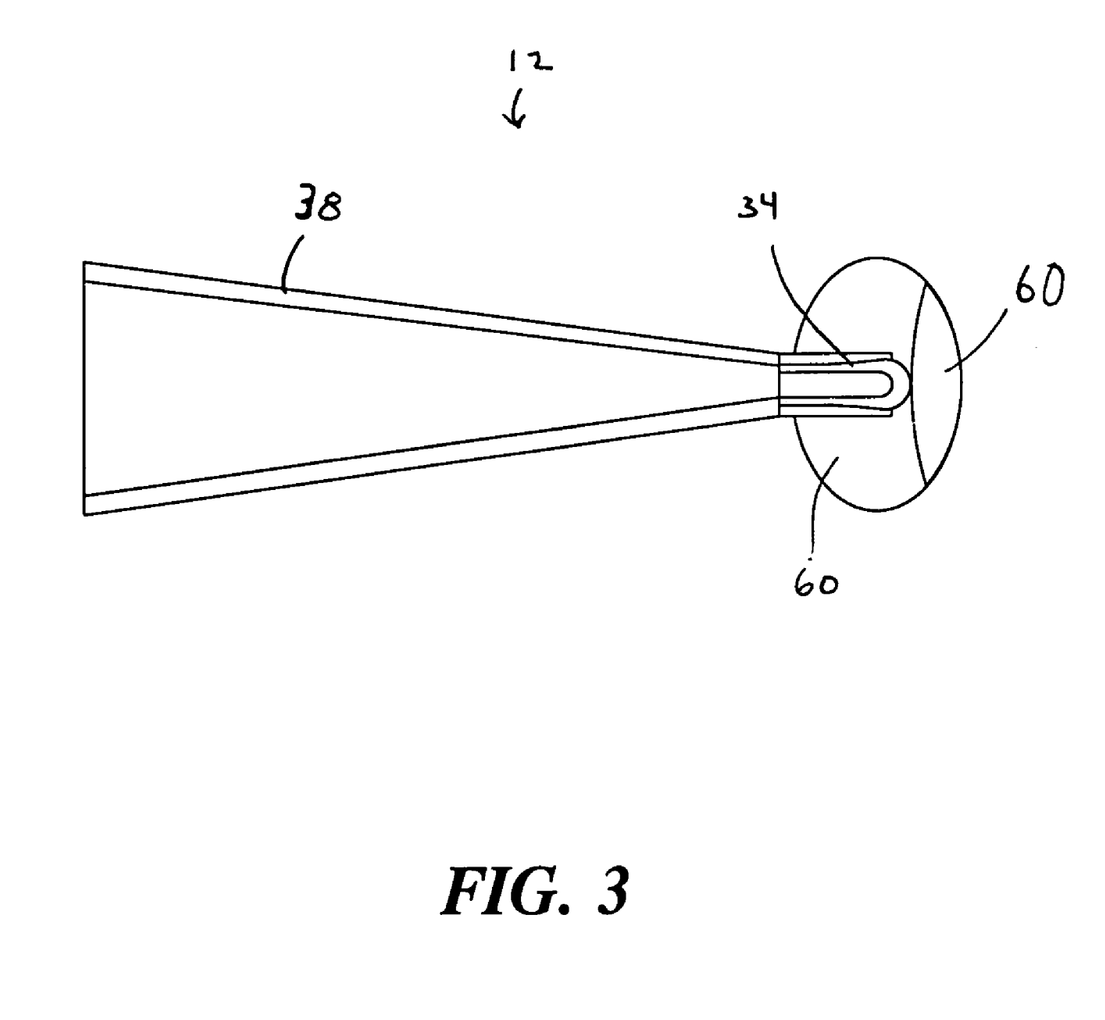
FIG. 3 is a diagrammatic view of the distal end of the applicator portion of the applicator system and the radiation shield of FIG. 2B coupled together.

A proximal end of the applicator head 30 is adapted to receive probe 48. As shown in FIG. 3, the applicator shank 38 includes an applicator barrel 32 which supports applicator head 30. In one form, applicator head 30 is integral with shank 38, and in other forms applicator head 30 is removable such that any of a number of heads can be used with a given shank. The applicator 12 may further include a low energy radiation filter 34 that is formed from a material that absorbs or blocks low energy radiation produced by the probe 48 in order to prevent adverse effects on tissue adjacent the applicator head 30. The shape of the low energy filter 34 is determined by the output profile of the radiation source in the radiation probe 48. Preferably, the shape of the low energy filter 34 is selected to reduce the low energy radiation produced outside the applicator head 30 to an acceptable level for the required treatment. For applicator systems with large applicator heads, a low energy filter may not be required because the applicator head may be sufficiently sized to attenuate the low energy radiation.

Preferably, the applicator 12 is formed from a biocompatible material such as Ultem-1000, a polyetherimide available from General Electric Plastics of Schenectady, N.Y. The shank 38 and barrel 32 are either molded or machined from a single piece of material and the filter 34 and the applicator head 30 can be fixed in place using a biocompatible epoxy (such as Epo-Tek 353-ND available from Epo-Tek of Billerica, Mass.). The applicator 12 can be formed (such as by molding or machining) from a single piece of material or from several pieces that are fastened together, such as by biocompatible epoxy. Preferably, the low energy filter is formed from an aluminum material. Preferably, the radiosurgery system 40 is a photonradiosurgery system (PRS) available from Photoelectron Corp. of Lexington, Mass.

The biocompatible radiation shield 60 can be formed from any biocompatible, radiation blocking or absorbing material. The biocompatible radiation shield 60 can be formed from a tungsten filled urethane material which can be approximately 60 to 90 percent tungsten by weight. In the preferred embodiment, the biocompatible radiation shield 60 is formed from a tungsten filled urethane material which is approximately 80 percent tungsten by weight. Alternatively, the biocompatible radiation shield 60 can be constructed from any known biocompatible material, such as silicone, polyamides, or polystyrenes, which can be filled with a radiation blocking or absorbing material, such as tungsten, gold, platinum, rhodium, iridium, tantalum or barium oxide. In the preferred embodiment, the tungsten filled urethane is a substantially flexible and is adapted, such as by preforming, to conform to the surface contour of the applicator head 30. Alternatively, as a person having ordinary skill in the art will appreciate, the biocompatible radiation shield can be formed from a substantially rigid material that is molded or preformed to conform to the surface contour of applicator head 30. In the preferred embodiment, the biocompatible radiation shield 60 is fastened to the surface of applicator head 30 by the natural adhesion of the tungsten filled urethane material. Alternatively, as a person having ordinary skill in the art will appreciate, any known biocompatible method of fastening the biocompatible radiation shield 60 to the surface of the applicator head 30 can be used, for example, biocompatible adhesives, small nails or tacks, and welding or fusing.

In the preferred embodiment, the biocompatible radiation shield 60 is formed from a thin sheet of tungsten filled urethane material by a thermoforming process. The thermoforming process includes heating the sheet of tungsten filled urethane material to a predetermined temperature whereby the sheet material can be shaped to conform to the surface contour of an applicator head 30. The predetermined temperature provides that the material is soft enough to be formed but does not flow or stick to the forming equipment. In the preferred embodiment, the tungsten filled urethane material is heated to 135 degrees centigrade for 45 minutes. The heated material is placed onto a form that shapes the material to conform to the surface contour of the applicator head 30 and cut to a predefined size. The formed, biocompatible radiation shield is allowed to cool at which point it retains a preformed shape which substantially conforms to the surface contour of the form and subsequently the applicator head 30.

Figure 4:
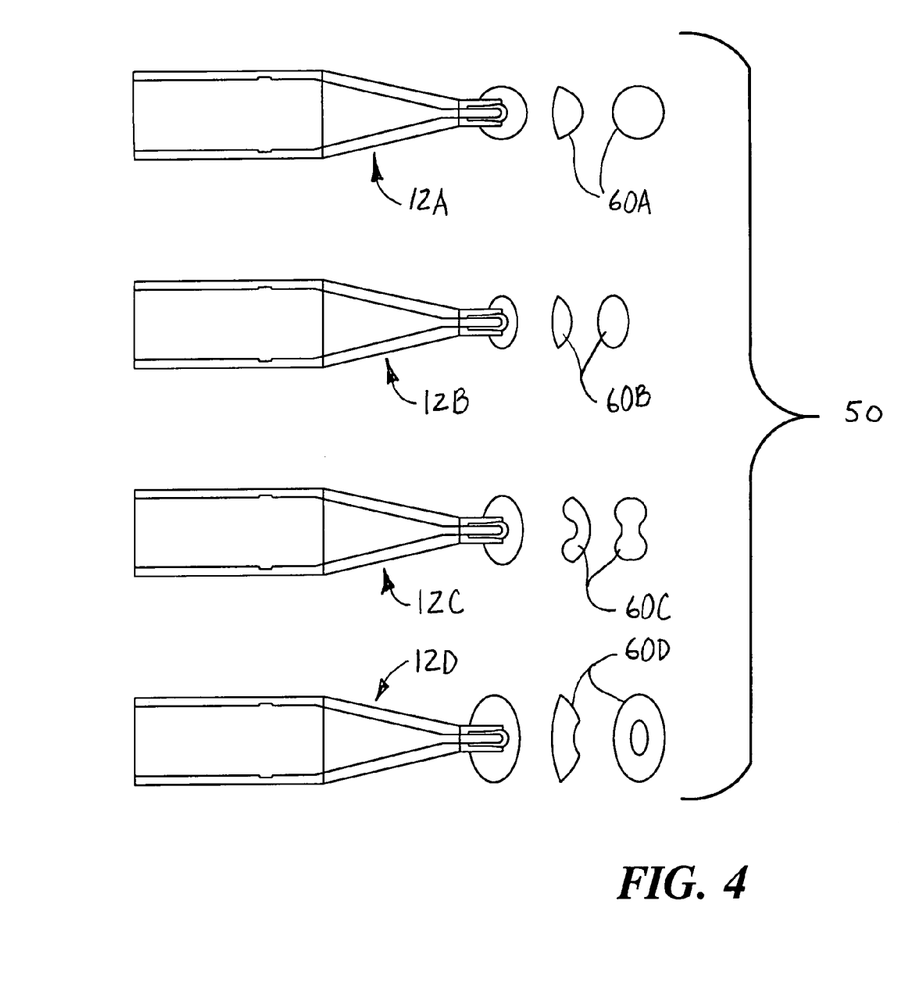
FIG. 4 is a diagrammatic cross sectional view of a plurality of applicator system applicators and radiation shields forming part of a kit, in accordance with another aspect of the invention.

FIG. 4 shows a kit 50 containing a plurality of applicators 12A–12D and corresponding shields 60A–60D. The kit also preferably includes an accompanying plurality of adapters 20 (not shown). Each applicator can include a different size and/or shaped applicator head 30 and a different size and/or shape biocompatible radiation shield 60 as may be used to treat multiple sites. In kit 50, applicator 12A includes a spherical shaped applicator head and biocompatible radiation shield and applicators 12B–12D include ellipsoidal shaped applicator heads of differing size. Applicator adapter 12B includes a substantially ellipsoidal shaped and contoured biocompatible radiation shield. Applicator adapter 12C includes a substantially ellipsoidal contoured and hour glass shaped biocompatible radiation shield. Applicator adapter 12D includes a substantially ellipsoidal shaped and contoured biocompatible radiation shield which includes a hole.

It is desirable for the radiation dose delivered across the surface of the applicator head to be substantially uniform over substantially its entire surface. For spherical surface applicator heads, this accomplished by selecting a radiation probe that produces a substantially spherical radiation dose profile. One method of producing ellipsoidal radiation dose profiles with ellipsoidal applicator heads is to use the density of the surface applicator material to filter the radiation and modify, for example, a spherical dose profile in order to produce an ellipsoidal dose profile. Where it is desirable to shield a location such as a vital organ from radiation, a biocompatible radiation shield 60 can be fastened to the applicator head in the location adjacent the area to be shielded. In addition, thin slits or small holes can be provided in the biocompatible radiation shield in order to further control or attenuate the dose of radiation applied to an area or volume.

Preferably, during treatment, the radiosurgery system 40 with the attached applicator system 10 is supported by a gimbal mounted support system such as that disclosed in commonly owned U.S. patent application Ser. No. 09/502,473, which is hereby incorporated by reference. This allows a physician applying treatment to guide the tip of the applicator without having to support the weight of the device for the duration of the treatment.

The above described system can be used to treat the site where a tumor or a portion of a tumor was removed with a predefined dose of radiation. The treatment involves inserting the applicator head with the biocompatible radiation shield fastened in position into the site and delivering a continuous or intermittent dose of radiation to the tissue adjacent the exterior surface of the applicator head. Preferably, the shape of the applicator head is selected to closely match the shape of the excised tumor in order to support the surrounding tissue and provide accurate application of the radiation dose.

The invention may be embodied in other specific forms without departing from the spirit or essential characteristics thereof. For example, the radiation shield could be made integral with the applicator head, rather than separate. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A biocompatible radiation shield for use with a radiation applicator system for a radiation source, said radiation applicator system including an applicator head defining a surface having a predefined shape and surface contour, said radiation shield comprising:

a substantially thin, biocompatible material, wherein said biocompatible material has a preformed shape conforming to the shape of at least a portion of the surface contour of said applicator head.

2. A biocompatible radiation shield according to claim 1 wherein said biocompatible material includes at least one radiation blocking or absorbing material chosen from the group including tungsten, gold, platinum, rhodium, iridium, tantalum and barium oxide.

3. A biocompatible radiation shield according to claim 1 wherein said biocompatible material includes at least one material chosen from the group including urethane, silicone polyamides, and polystyrenes.

4. A biocompatible radiation shield according to claim 1 wherein at least a portion of said biocompatible material is characterized by an adhesiveness sufficient to allow the radiation shield to be coupled to said applicator head.

5. A biocompatible radiation shield according to claim 1, wherein the biocompatible radiation shield is formed from a tungsten filled urethane material including approximately 60 to 90 percent tungsten by weight.

6. A biocompatible radiation shield according to claim 5, wherein the biocompatible radiation shield is formed from a tungsten filled urethane material including approximately 80 percent tungsten by weight.

7. A radiation applicator system for use with a radiation source for facilitating the application of a dose of radiation to a volume, said radiation applicator system comprising:
   A) an applicator, substantially encasing a radiating probe of said radiation source, said applicator including:
      i) a shank having a proximal end and a distal end; and
      ii) a head secured to said shank distal end and defining a surface for engaging said volume to receive said dose of radiation; and
   B) an adapter, including:
      i) a first coupler suited for mated engagement with said shank proximal end; and
      ii) a second coupler suited for mated engagement with said radiation source; and
   C) a biocompatible radiation shield coupled to at least a portion of said head.

8. A radiation applicator system according to claim 7 wherein:
   said radiation source includes a housing having an elongated probe extending from said housing and said probe is adapted for producing predefined dose profiles of radiation at a distal end of said probe; and
   said head is adapted for receiving said distal end of said probe whereby radiation produced by said probe can be applied to an area adjacent said surface of said head.

9. A radiation applicator system according to claim 7 wherein said applicator head defines a substantially spherical surface and said biocompatible radiation shield is formed in the shape of at least a portion of said substantially spherical surface.

10. A radiation applicator system according to claim 7 wherein said applicator head defines a substantially ellipsoidal surface and said biocompatible radiation shield is formed in the shape of at least a portion of said substantially ellipsoidal surface.

11. A radiation applicator system according to claim 7 wherein said applicator head defines a substantially cylindrical surface and said biocompatible radiation shield is formed in the shape of at least a portion of said substantially cylindrical surface.

12. A radiation applicator system according to claim 7 further comprising a low energy filter, coupled to said distal end of the radiation applicator, for attenuating low energy radiation emitted from said probe.

13. A radiation applicator system according to claim 7 wherein said shank includes a fastening element adapted for fastening said applicator to said radiation source at first predefined position with respect to said radiation source.

14. A radiation applicator system according to claim 7 wherein the biocompatible radiation shield is formed from a tungsten filled urethane material including approximately 60 to 90 percent tungsten by weight.

15. A kit for applying radiation to a volume, said kit comprising:
   a radiation source adapted for producing a predefine radiation dose profile;
   a plurality of applicator systems and a corresponding plurality of biocompatible radiation shields, each of said applicator systems including:
      A) an applicator, substantially encasing a radiating probe of said radiation source, said applicator including:
         i) a shank having a proximal end and a distal end; and
         ii) a head secured to said shank distal end and defining a surface for engaging said volume to receive said dose of radiation; and
      B) an adapter, including:
         i) a first coupler suited for mated engagement with said shank proximal end; and
         ii) a second coupler suited for mated engagement with said radiation source; and
      C) a biocompatible radiation shield coupled to at least a portion of said head.

16. A kit according to claim 15 wherein the applicator head of at least one of the plurality of applicator systems is different in size or shape than the applicator head of at least one of the other applicator systems from the plurality of applicator systems.

17. A kit according to claim 15 wherein at least one of the plurality of radiation shields is different in size or shape than at least one of the other radiation shields.

18. A kit according to claim 15 wherein the applicator head of each of the plurality of applicator systems is different in size or shape than the applicator head of each of the other applicator systems.

19. A kit according to claim 15 wherein each of the plurality of radiation shields is different in size or shape than the other radiation shields.

20. A kit according to claim 15 wherein at least one of said biocompatible radiation shields includes at least one radiation blocking or absorbing material chosen from group including tungsten, gold, platinum, rhodium, iridium, tantalum, and barium.

* * * * *